United States Patent
Dowben et al.

(10) Patent No.: US 9,324,960 B2
(45) Date of Patent: Apr. 26, 2016

(54) SEMICONDUCTING ALLOY POLYMERS FORMED FROM ORTHOCARBORANE AND 1,4-DIAMINOBENZENE

(75) Inventors: Peter Dowben, Lincoln, NE (US); Jeffry Kelber, Denton, TX (US)

(73) Assignee: QUANTUM DEVICES, LLC, Rockville, MD (US)

( * ) Notice: Subject to any disclaimer, the term of this patent is extended or adjusted under 35 U.S.C. 154(b) by 161 days.

(21) Appl. No.: 14/115,104

(22) PCT Filed: Jun. 4, 2012

(86) PCT No.: PCT/US2012/040681
§ 371 (c)(1),
(2), (4) Date: Apr. 9, 2014

(87) PCT Pub. No.: WO2012/170330
PCT Pub. Date: Dec. 13, 2012

(65) Prior Publication Data
US 2014/0217375 A1     Aug. 7, 2014

Related U.S. Application Data

(60) Provisional application No. 61/494,610, filed on Jun. 8, 2011.

(51) Int. Cl.
C07F 5/02     (2006.01)
H01L 51/42    (2006.01)
H01L 51/00    (2006.01)

(52) U.S. Cl.
CPC ............ H01L 51/4213 (2013.01); C07F 5/027 (2013.01); H01L 51/0043 (2013.01)

(58) Field of Classification Search
None
See application file for complete search history.

(56) References Cited

U.S. PATENT DOCUMENTS

| | | | |
|---|---|---|---|
| 3,850,820 A | 11/1974 | Korshak et al. | |
| 3,896,083 A | 7/1975 | Gerber | |
| 4,076,634 A | 2/1978 | Korshak et al. | |
| 5,955,586 A | 9/1999 | Sessler et al. | |
| 6,248,916 B1 * | 6/2001 | Kane et al. | 558/72 |
| 6,771,730 B1 * | 8/2004 | Dowben et al. | 376/155 |
| 7,368,794 B2 * | 5/2008 | Caruso et al. | 257/428 |
| 2005/0180917 A1 | 8/2005 | Patel | |
| 2005/0202338 A1 | 9/2005 | Hawker et al. | |
| 2013/0233368 A1 * | 9/2013 | Dowben | 136/205 |
| 2014/0203382 A1 * | 7/2014 | Kelber et al. | 257/421 |

OTHER PUBLICATIONS

Pasquale, F., Liu, J., Dowen, P., and Kelber, J. (Mat. Chem. and Phys., 133 (2012), 901-906.).*
Pasquale, F., and Kelber, J. (App. Surf. Sci., 258 (2012), 2639-2642.).*
Luo, G., Lu, J., Liu, J., Mei, W. and Dowben, P. (Mat. Sci. and Eng. B, 175 (2010), 1-8.).*
Jacobsohn, L. G.; Schulze, R. K.; da Costa, M. E. H. Mala; Nastasi, M. Surf. Sci. 2004, 572, 418.
Bao, R.; Chrisey, D., B. Thin Sol. Films 2010, 519, 164.
Bernard, L.; Caruso, A. N.; Xu, B.; Doudin, B.; Dowben, P. A. Thin Sol. Films 2003, 428, 253.
Ruhl, E.; Hitchock, A. P.; Bozek, J. D.; Tyliszczak, T.; Kilcoyne, A. L. D.; McIlroy, D. N.; Knop-Gericke, A.; Dowben, P. A. Phys. Stat. Sol. B 2009, 246, 1496.
Zharnikov, M.; Grunze, M., J. Vac. Sci. Technol. B 2002, 20, 1793-1807.
Geyer, W.; Stadler, V.; Eck, W. Zharnikov, M.; Golzhauser, A.; Grunze, M. Appl. Phys. Lett. 1999, 75, 2401-2403.
Eck, W.; Stadler, V.; Geyer, W.; Zharnikov, M.; Golzhaüser, A.; Grunze, M. Adv. Mater. 2000, 12, 805-808.
Werheit, H. J. Phys. : Conf. Ser. 2009, 176, 012019.
Search Report and Written Opinion received in PCT Application No. PCT/US2012/040681, dated Aug. 21, 2012.
International Preliminary Report on Patentability and Written Opinion received in PCT Application No. PCT/US2012/040681, dated Dec. 27, 2013.
Fox, M. A.; Hughes, A. K. Coord. Chem. Rev. 2004, 248, 457.
Ahmad, A., A.; Ianno, N. J.; Snyder, P. G.; Welipitiya, D.; Byun, D.; Dowben, P. A. J. Appl. Phys. 1996, 79, 8643.
Behera, S.; Wilks, J.; Dowben, P. A.; Kelber, J. A. Surf. Sci. 2010, 604, L51.
Caruso, A. N.; Balaz, S.; Xu, B.; Dowben, P. A.; McMullen-Gunn, A. S.; Brand, J. I.; Losovyj, Y. B.; McIlroy, D. N. App. Phys. Lett. 2004, 84, 1302.
Farha, O. K.; Spokony, A. M.; Mulfort, K. L.; Hawthorne, F. M.; Mirkin, C. A.; Hupp, J. T. J. Am. Chem. Soc. 2007, 129, 12680.
Schwab, P. F. H.; Levin, M. D.; Michl, J. Chem. Rev. 1999, 99, 1863.
Sevryugina, Y.; Julius, R.; Hawthorne, M. F. Inorg. Chem. 2010, 49, 10627.
Yang, X.; Jiang, W.; Knobler, C. B.; Mortimer, M. D.; Hawthorne, M. F. Inorg. Chem. 1995, 240, 371.
Yang, X.; Jiang, W.; Knobler, C. B.; Hawthorne, M. F. J. Am. Chem. Soc. 1992, 114, 9719.
Caruso, A. N.; Dowben, P. A.; Balkir, S.; Schemm, N.; Osberg, K.; Fairchild, R. W.; Flores, O. B.; Balaz, S.; Harken, A. D.; Robertson, B. W.; Brand, J. I. Mat. Sci. and Eng. 2006, 135, 129.
Robertson, B. W.; Adenwalla, S.; Harken, A.; Welsch, P.; Brand, J. I.; Dowben, P. A.; Claassen, J. P. App. Phys. Lett. 2002, 80, 3644.
Emin, D.; Aselage, T. J. App. Phys. 2005, 97, 013529.
Day, E.; Diaz, M. J.; Adenwalla, S. J. Phys. D.: Appl. Phys. 2006, 39, 2920.
Caruso, A. N. J. Phys. : Cond. Matt. 2010, 22, 443201.

(Continued)

*Primary Examiner* — Kevin Bernatz
(74) *Attorney, Agent, or Firm* — Steven B. Kelber; The Kelber Law Group

(57) ABSTRACT

Novel semiconducting polymers have been formed via the electron-induced cross-linking of orthocarborane B10C2H2 and 1,4-diaminobenzene. The films were formed by co-condensation of the molecular precursors and 200 eV electron-induced cross-linking under ultra-high vacuum (UHV) conditions. Ultraviolet photoemission spectra show that the compound films display a shift of the valence band maximum from ~4.3 eV below the Fermi level for pure boron carbide to −1.7 eV below the Fermi level when diaminobenzene is added. The surface photovoltage effect decreases with decreasing B/N atomic ratio. A neutron detector comprises the polymer as the p-type semiconductor to be paired with an n-type semiconductor.

14 Claims, 5 Drawing Sheets

(56) References Cited

OTHER PUBLICATIONS

Caruso, A. N.; Billa, R. B.; Balaz, S.; Brand, J. I.; Dowben, P. A. J. Phys.: Cond. Matt. 2004, 16, L139.

Osberg, K.; Schemm, N.; Balkir, S.; Brand, J. I.; Halbeck, M. S.; Dowben, P. A.; Hoffman, M. W. IEEE Sens. J. 2006, 6, 1531.

Osberg, K.;Schemm, N.;Balkir, S.;Brand, J.;Halbeck, S.; Dowben, P. Proceedings of the 2006 IEEE Symposium on Circuits and Systems (ICAS 2006) 2006, 1179.

Mortensen, M. W.; Sørensen, P. G.; Björkdahl, O.; Jensen, M. R.; Gundersen, H. J. G.; Bjørnholm, T. App!. Rad. and Isotopes 2006, 64, 315.

Luo, G.; Lu, J.; Liu, J.; Mein, W.; Dowben, P. A. Mat. Sci. and Eng. B 2010, 175, 1.

Von Wrochem, F.; Scholz, F.; Gao, D.; Nothofer, H.; Yasuda, A.; Wessels, J. M.; Roy, S.; Chen, X; and Michl, J. J. Phys. Chem. Lett. 2010, 3471, 3477.

Hwang, S.; Remmes, N. B.; Dowben, P. A.; McIlroy, D. N. J. Vac. Sci. and Technol. B 1996, 14, 2957.

Hwang, S.; Remmes, N.; Dowben, P. A.; McIlroy, D. N. J. Vac. Sci. and Technol. A 1997, 15, 854.

Carlson, L.; Lagraffe, D.; Balaz, S.; Ignatove, A.; Losovyj, Y. B.; Choi, J.; Dowben, P. A.; Brand, J. I. Appl. Phys. A. 2007, 89, 195.

Dowben, P. A.; Kizilkaya, O.; Liu, J.; Montag, B.; Nelson, K.; Sabirianov, I.; Brand, J. I. Mat. Lett. 2009, 63, 72.

McIlroy, D. N.; Hwang, S. D.; Yang, K.; Remmes, N.; Dowben, P. A.; Ahmad, A. A.; Ianno, N. J.; Li, J. Z.; Lin, J. Y.; Jiang, H. X. Appl. Phys. A. 1998, 67, 335.

Liu, J.; Luo, G.; Mei, W.; Kizilkaya, O.; Shepherd, E. D.; Brand, J. I.; Dowben, P. A. J. Phys. D.: Appl. Phys. 2010, 43, 085403.

Carroll, R. L; Gorman, C. B. Angew. Chem. Int. Ed. 2002, 41, 4378.

McIlroy, D. N.; Zhang, J.; Dowben, P. A.; Xu, P.; Heskett, D. Surf. Sci. 1995, 328, 47.

Zhang, J.; McIlroy, D. N.; Dowben, P. A.; Zeng, H.; Vidali, G.; Heskett, D.; Onellion, M. J. Phys. Cond. Matt.1995, 7, 7185.

McIlroy, D. N.; Zhang, J.; Dowben, P. A.; Heskett, D. Mat. Sci. and Eng. A. 1996, 217/218, 64.

Caruso, A. N.; Bernard, L; Xu, B.; Dowben, P. A. J. Phys. Chem. B. 2003, 107, 9620.

Balaz, S.; Caruso, A. N.; Platt, N. P.; Dimtcho, I. D.; Boag, N. M.; Brand, J. I.; Losovyj, Y. B.; Dowben, P. A. J. Phys. Chem. B 2007, 111, 7009.

Ruhl, E.; Riehs, N.; Behera, S.; Wilks, J.; Liu, J.; Joachim, H. —.; Caruso, A. N.; Boag, N. M.; Kelber, J. A.; and Dowben, P. A. J. Phys. Chem. A. 2010, 114, 7284.

Werheit, H. J. Phys.: Cond. Matt. 2007, 19, 186207.

Hwang, S.; Yang, K.; Dowben, P. A.; Ahmad, A. A.; Ianno, N. J.; Li, J. Z.; Lin, J. Y.; Jiang, H. X.; McIlroy, D. N. Appl. Phys. Lett.1997, 70, 1028.

Lee, S.; Mazurowski, J.; Ramseyer, G.; Dowben, P. A. J. Appl. Phys. 1992, 72, 4925.

Lunca-Popa, P.; Brand, J. I.; Balaz, S.; Rosa, L. G.; Boag, N. M.; Bai, M.; Robertson, B. W.; Dowben, P. A. J. Phys. D. : Appl. Phys. 2005, 38, 1248.

Pasquale, F.; Kelber, J., Appl. Surf. Sci. 2012, 258, 2639.

Moulder, J. F., Stickle, W. F., Sobol, P. E.; Bomben, K. D. Handbook of X-ray Photoelectron Spectroscopy; Physical Electronics: Eden Prairie, Minnesota, 1995.

Tanuma, S.; Powell, C. J.; Penn, D. R. Surface and Interface Analysis 2003, 35, 268.

Practical Surface Analysis, 2nd ed; Briggs, D. Seah, M. P., Eds.; Auger and X-ray Photoelectron Spectroscopy vol. 1; John Wiley and Sons, INC.: New York, USA, 1990; vol. 1, pp. 244-248.

Feng, D.-Q.; Losovyj, Y.; Tai, Y.; Zharnikov, M.; Dowben, P. J. Mater. Chem. 2006, 16, 4343.

Xiao, J.; Zhang, Z.; Wu, D.; Routaboul, L; Braunstein, P.; Doudin, B.; Losvyj, Y. B.; Kizilkaya, O.; Rosa, L., G.; Borca, C. N.; Gruverman, A.; Dowben, P. A. Phys. Chem. Chem. Phys. 2010, 12, 10329.

Xiao, J.; Dowben, P. A. J. Phys.: Cond. Matt. 2009, 21, 052001.

Xiao, J.; Sokolov, A.; Dowben, P. A. Appl. Phys. Lett. 2007, 90, 242907.

Dowben, P. A.; Rosa, L. G.; Hie, C. C.; Xiao, J. J. Elect. Spect. and Rel. Phenom. 2009, 174, 10.

Xiao, J.; Dowben, P. A. J. Mater. Chem. 2009, 19, 2172.

Zhang, Z.; Alvira, J.; Barbarosa, X.; Rosa, L., G.; Routaboul, L.; Braunstein, P.; Doudin, B.; Dowben, P. A. J. Phys. Chem. C. 2011, 115, 2812.

Feng, D.-Q.; Wisbey, D.; Losovyj, Y. B.; Tai, Y.; Zharnikov, M.; Dowben, P. A. Phys. Rev. B. 2006, 74, 165425.

Jimenez, I.; Sutherland, D. G. J.; van Buren, T.; Carlisle, J. A.; Terminello, L. J.; Himpsel, F. J. Phys. Rev. B 1998, 57, 13167.

\* cited by examiner

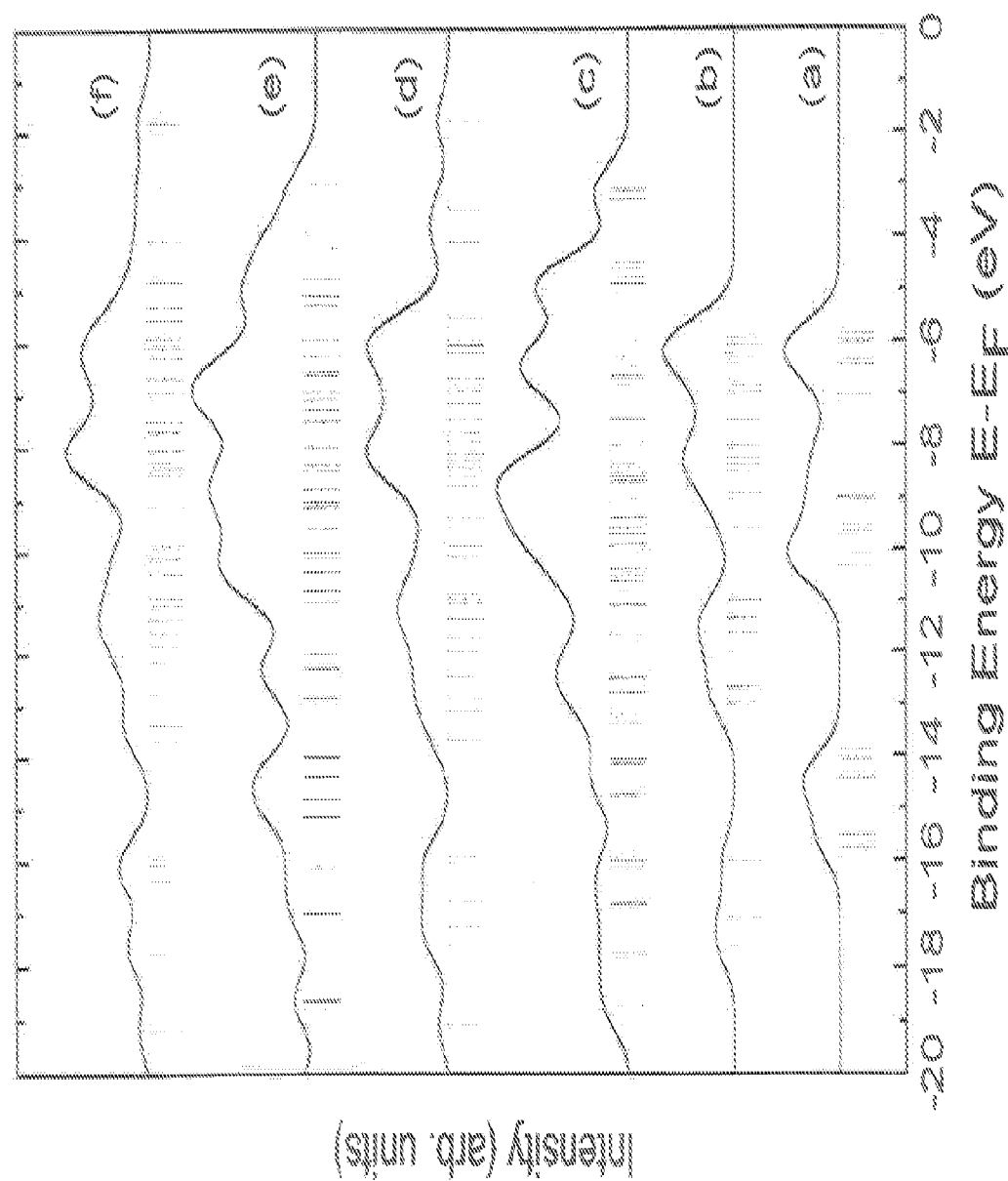

SEMICONDUCTING ALLOY POLYMERS FORMED FROM ORTHOCARBORANE AND 1,4-DIAMINOBENZENE

PRIORITY DATA AND INCORPORATION BY REFERENCE

This application is a National Stage entry under 35 U.S.C. 371 of PCT/US2012/040681, filed on Jun. 4, 2012, which claims priority to U.S. Provisional Patent Application Ser. No. 61/494,610, filed Jun. 8, 2011, the entireties of which are hereby incorporated by reference.

This work was supported by the Defense Threat Reduction Agency (DTRA) Grant Number: HDTRA1-09-1-0060.

BACKGROUND OF THE INVENTION

1. Field of the Invention

This invention pertains to the formation of new thin films and alloys prepared from orthocarborane and 1,4 diaminobenzene, and those films and their properties, as well as the devices that can be prepared with those thin materials.

2. Background of the Invention

Materials based on carborane icosahedra $B_{10}C_2H_{12}$ are of broad interest in such areas as the fabrication of semiconducting boron carbides $B_{10}C_2H_{12}$ for hydrogen absorption and storage,[5] novel molecular architectures,[5-9] all-boron carbide neutron detectors,[10-17] biomedical applications,[18] and recently, spintronics[19] and molecular electronics.[20] In many of these applications, the ability to systematically vary the valence electronic structure and properties of the material by doping[21-26] or incorporation of other molecular species[27] is of obvious interest.

The alloy polymers of the invention—true alloys rather than co-deposited materials or a doped film, find application in all of the above-described devices. The relevant disclosures of references 5-20, set forth at the end of the specification of this application, are incorporated herein—by reference, for the purposes of informing the reader of the level of skill in the art in the preparation of those devices. The application of these materials in a portable, high sensitivity, solid state neutron detector is exemplified herein, but the invention lies in the alloy polymer itself, the properties resulting therefrom and the devices that advantageously benefit from those properties.

SUMMARY OF THE INVENTION

We have developed a novel polymer. The altered electronic properties of a novel polymer formed by electron-beam cross-linking of ortho-carborane with 1,4-diaminobenzene (DAB) offer wide applicability within the field of electronics and solid state technology. $B_{10}C_2H_x$ films are generally wide band gap semiconductors[2, 20, 21] due to the high ionization potential of carboranes[22]. Spintronic and logic devices will benefit from these materials. Recently reported valence band photoemission results for self-assembled monolayers of carborane/thiol hybrids on Au(111) indicate that this characteristic dominates the electronic structure, resulting in a valence band maximum ~4.3 eV below the Fermi level[16], similar to results for pure $B_{10}C_2H_x$ films derived from entirely from orthocarborane precursors[14]. In contrast, alloyed boron carbide/diaminobenzene films formed in our experiments (B/N atomic ratio ~4-4.9) exhibit a valence band maximum at 1.7 eV or less below the Fermi level. Additionally, the results reported here indicate that the bonding between orthocarborane icosahedra and DAB involve bonds between DAB carbon sites and boron sites bound only to other borons (B-B-H sites) as opposed to C-B-H or C-H sites on the icosahedra. The resulting electronic properties are indicative of a true alloyed material, rather than the sum of non-interacting orthocarborane and DAB moieties.

Neutron and other similar heavy particle detectors present an increasingly important component of national safety and security. Ideally, handheld solid-state detectors will allow inspectors to track the shipment of radioactive materials intra-state and inter-state. There is ideally a method by which every ship entering every harbor in the United States, and every vehicle crossing every national boundary, as well as truck weigh stations distributed throughout the National highway system, can be monitored, so that the safety of known shipments of radioactive materials can be documented, and the introduction of unwanted materials can be kept from elements adverse to the interests of a nation. A solid state detector, which permitted both qualitative (i.e., there is radioactive material present) and quantitative (how much material is present) outputs would advance these interests significantly. Representative neutron detectors are disclosed in U.S. Pat. Nos. 6,771,730 and 7,368,794, both of which are incorporated herein-by-reference.

To make a neutron detector solid state device it important not only to have neutron capture and a charge signal produced in a semiconductor, but also to extract the charge from the device. Given that the semiconductor device should be thirty (30) microns thick to be opaque to thermal neutrons, this is a rather large depletion region for charge extraction. One way to improve the signal to noise ratio to get better extraction is to create more efficient charge separation (electron-hole separation) and thus a bigger current pulse. The alloy of the invention, of orthocarborane doped with 1,4-diamionobenzene has the disadvantage that the device depletion region has to be increased from 30 microns to 45-50 microns, but the very significant charge separation means much better charge extraction from the device which is a huge advantage.

In applications where neutron voltaic capabilities are sought (current generation at zero bias), the improved charge separation will lead to improved zero bias current. At such a low power cost, a neutron voltaic type sensor would be a useful tool for passive sensor array detectors for monitoring special nuclear materials for treaty verification and stewardship of the legacy stockpile, not to mention tagging of waste radioactive materials with high neutron emission signatures. One may tag the device to the special nuclear materials—the neutron signature powers the device through current production, not as a photovoltaic but as a neutron Voltaic—separation from the source would cause the signal to cease (thus creating a reason to flag the sensor network), and if multiplexed, movement would also flag the network.

The novel alloy films of the invention exhibit smaller band gaps and greater electron-hole separation lifetimes, as the novel linking units decrease the binding energy of the valence band maximum below the Fermi level, and the top of the valence band consists of states localized on the linking unit, so the bottom of the conduction band should have states associated with the carborane unit. The improved conductivity and related characteristics of these materials lend themselves to the preparation of solid state neutron detectors, and many other devices.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 5. Comparison of model calculations for molecular density of states based on the closo-1,2-ortho-carborane molecule (a,b), ortho-carborane-DAB linked molecule in single boron-carbon bridge bonding configuration (c,d), ortho-carborane-DAB molecule (e,f) linked by a double boron to carbon bridge bonding configuration. The density of states was estimated by applying 1 eV Gaussian widths to the molecular orbital eigenvalues (vertical lines) obtained from both a PM3 (parameterized method 3) semi-empirical approach (a, c, e) and density functional theory (DFT) with the hybrid function B3LYP and the 6-13G* basis (b, d, f).

DETAILED DESCRIPTION OF THE INVENTION

Experimental Methods

Figure 1:
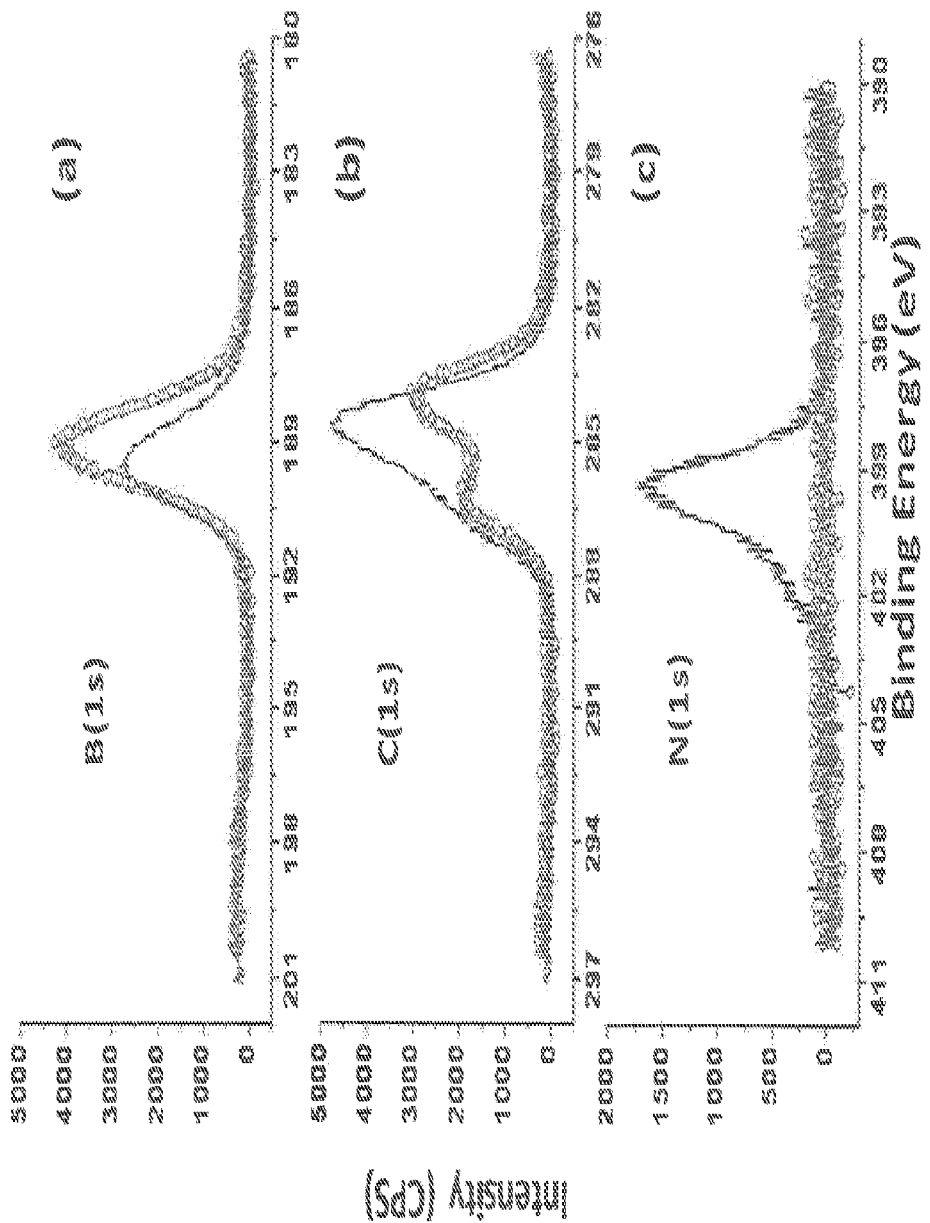
FIG. 1 is (a) B(1s), (b) C(1s) and (c) N(1s) core level spectra for a 90 Å thick pure boron carbide film (open circles), and a 90 Å thick boron carbide/DAB film (solid red line) with a B/N atomic ratio of 4.9. Spectra acquired a room temperature.

Experiments were carried out in a UHV system that has been described previously.[38] Briefly, the system had a base pressure of $3\times10^{-10}$ Torr, and was equipped with a 140 mm mean radius hemispherical analyzer and channel plate detector. XPS spectra were acquired with a commercially available unmonochromatic $_{A1k\alpha}$ x-ray source. UPS spectra were acquired with a commercial, differentially-pumped discharge source, using He I excitation (21.2 eV). XPS and UPS spectra were acquired in the constant pass energy mode with pass energies of 23.5 eV and 2.95 eV, respectively. The system was also equipped with an Ar ion sputter gun and commercial electron gun for e-beam induced cross-linking. The sample manipulator allowed for sample heating or cooling between 1000 K and 110 K by a combination of resistive heating and liquid $N_2$ cooling. Sample temperature was monitored with a type K thermocouple in proximity to the sample.

Ortho-carborane and 1,4-diaminobenzene (spectral grade) were obtained from commercial sources, then purified by freeze-pump-thaw procedures and admitted into the UHV chamber via separate manual leak valves. For ortho-carborane and 1,4-diaminobenzene sublimation into UHV, the precursor glass containers, stainless steel gas lines, and manual leak valves were heated to ~330 K and ~350K, respectively. Pressures in the chamber were monitored using a nude ion gauge out of the line of site to the sample. Ortho-carborane and 1,4-diaminobenzene (DAB) exposures are reported here in terms of Langmuir (L) ($1L=10^{-6}$ Torr-sec) and have not been corrected for ion gauge sensitivity or flux to the sample surface.

Films were formed by condensing precursors onto a 1×1 $cm^2$ copper foil cooled to 110 K under UHV conditions. Cross-linking was carried out by a 200 eV electron beam using the electron gun set to a constant emission current. This approach has proven effective in similar experiments.[23] Electron flux to the surface was not measured directly. XPS and UPS spectra were acquired before/after cross-linking at 110 K and after subsequent warm up to 300 K.

Spectra were referenced to a $Cu_{(2p3/2)}$ binding energy of 932.7 eV.[39] The thicknesses of the deposited films (d) were estimated according to:

$$I=I_0\exp(-d/\lambda)$$

where $\lambda$ is the calculated[40] inelastic mean free path of 14.88 Å for a $Cu_{(2p3/2)}$ electron through a $B_{10}C_2H_x$ film. Relative atomic concentrations were determined according to:[39, 41]

$$N_x/N_y=(I_x/I_y)(A_y/A_x)$$

where $N_x$, and $N_y$ are the atomic concentrations of species x and y; $I_x$, $I_y$ are corresponding integrated core level peak intensities, and $A_x$, $A_y$ are the corresponding atomic sensitivity factors (corrections that include the analyzer transmission function) appropriate to this analyzer.[39] The use of absolute, rather than relative experimental intensities in (1) and (2) introduces some potential error due to slight fluctuations in x-ray flux and sample position, but experience with this analyzer indicates that such error may be conservatively estimated at <10%.

The Theoretical Approaches

The orbital energies of the single molecules were calculated using both the semiempirical (PM3) and the hybrid density function theory (DFT B3LYP) methods, as has been undertaken successfully elsewhere.[32,42-49] Geometric optimization of the system was performed by obtaining the lowest unrestricted Hartree-Fock (UHF) energy states. DFT calculations were done with the Spartan package 06, with the standard 6-31 G* basis set. A model density of states was obtained by applying equal Gaussian envelopes of 1 eV width to each molecular orbital at the ground state binding energies to account for the solid state broadening in photoemission and then summing together with a rigid energy shift of a typical value of 5 eV and 2.7 eV applied to the calculated electronic structure by PM3 and DFT, respectively. In the case of the semiempirical calculation, much of this shift takes into account the work function.

Results

Core and Valence Band Spectra

B(1s), C(1s), and N(1s) spectra acquired at room temperature are displayed in FIG. 1 for a film composed solely of cross-linked ortho-carborane (open circles), and an ortho-carborane/DAB film (solid red line). Both films have an estimated film thickness of 90 Å, and the ortho-carborane/DAB compound film has a B/N ratio of 4.9, indicating equal concentrations of ortho-carborane and DAB moieties in the film. Small amounts of O(1s) core level photoemission intensity (not shown) were observed for both pure ortho-carborane and the compound films. The total oxygen core level photoemission intensities were small and variable from experiment to experiment, indicating that the oxygen was most likely due to incidental OH/O condensation and incorporation during cross-linking at low temperature. Independent measurements confirm this.

The B(1s) and C(1s) photoemission spectra for the pure carborane film (FIG. 1 a,b) are typical of those observed for $B_{10}C_2H_x$ films[3, 50-52] as well as condensed ortho-carborane multilayers.[53] The B(1s) peak maximum is near 189 eV and is composed of bonding environments due to B-B-H species and (at a higher binding energy) C-B-H species.[3, 50] The C(1s) spectrum (FIG. 1b, open circles) features two peaks, with the one at lower binding energy attributed to carbon atoms within the icosahedron and the one at higher binding energy indicative of graphitic or contaminant carbon.[50,52] In contrast, the B(1s) spectrum of the composite film (FIG. 1a, solid red line) is significantly narrower than that of the ortho-carborane film, with the lower binding energy region attributable to B-B-H sites absent from the spectrum. The C(1s) spectrum of the composite film (FIG. 1b, red line) has a C(1s) spectrum with similar width and peak maximum identical in binding energy to that of condensed DAB (not shown), but with a lower binding energy region similar to that of the ortho-carborane film and consistent with carbon atoms bonded to boron atoms. The N(1s) spectrum of the composite film (FIG. 1c, solid red line) exhibits a peak maximum identical to that of condensed DAB film (not shown), but with a small, higher binding energy shoulder that may indicate some nitrogen bonding to contaminant oxygen or OH species in the film.

The B(1s) photoemission spectrum of the composite film (FIG. 1a,b) indicates that bonding between carborane and DAB units in the compound film occur at B-B-H sites in the ortho-carborane icosahedra, as intensity from this region is absent from the B(1s) spectrum of the composite film. Further, the lack of significant perturbation of the N(1s) core level spectra from that of condensed DAB indicates that the N sites are not perturbed by the cross-linking process. The core level spectra of the carborane, condensed DAB, and composite films (FIG. 1) therefore indicate that the composite film is composed of carborane icosahedra bonded to intact DAB species predominantly via B-B-H sites on the icosahedra and the carbon sites on the DAB units.

Figure 2:
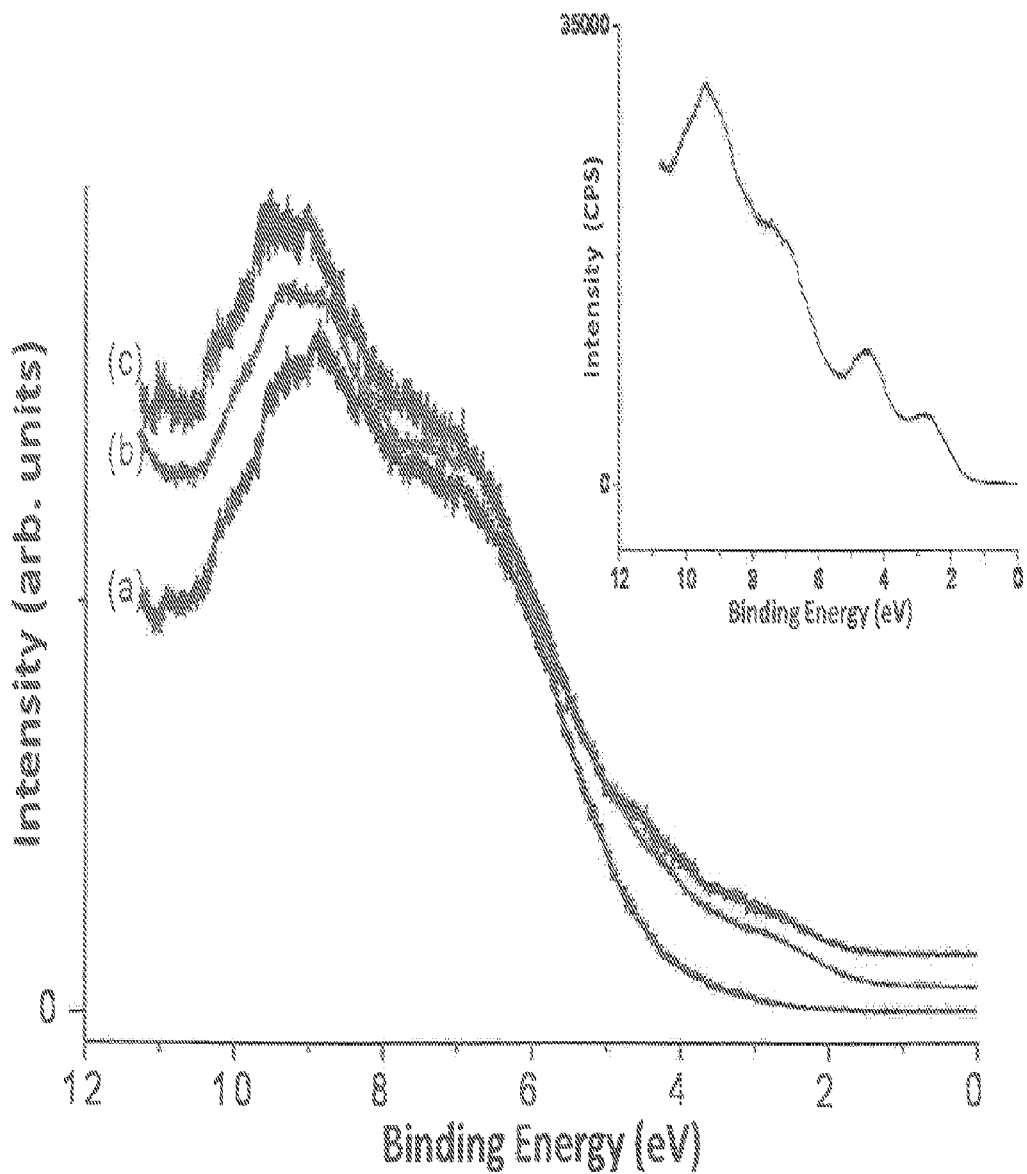
FIG. 2. UPS spectra for (a) a 90 Å thick ortho-carborane film (same film as in FIG. 1); (b) 90 Å thick composite film FIG. 3. UPS spectra: Surface photovoltage effect for (a) orthocarborane film (50 Å thick) and (b) composite film (80 Å thick, B/N atomic ratio 3.5) condensed at 110 K before (i) and after (ii) electron-induced cross-linking.

The UPS spectra of the 90 Å thick ortho-carborane and composite films are compared in FIG. 2 with that of a second composite film with a B/N atomic ratio of 4.0 (N-rich) and an average thickness of 40 Å. The UPS spectra have been normalized to have equal intensities at 7.5 eV binding energy in order to facilitate the comparison of spectral shapes. The spectrum of the carborane film (FIG. 2, black line) is similar to those reported previously[4, 20] with a valence band maximum near 4.3 eV. In contrast, the spectra of both the 90 Å thick and 40 Å thick composite films (FIG. 2, red, and blue traces, respectively) show the presence of states significantly closer the Fermi level, with valence band maxima near 1.7 eV below the Fermi level. The general correspondence of the spectra of both composite films indicates that the spectral features at binding energies <4.3 eV are relatively insensitive to film thickness or precise B/N atomic ratio. That this region of the spectrum is so similar for both composite films also indicates no observable contribution from the valence band of the Cu substrate.

A comparison of the UPS spectra of the composite and carborane films (FIG. 2) indicates that the spectra of the composite film at binding energies >~4.3 eV are dominated by states associated with the ortho-carborane icosahedra. A comparison of the spectra of the composite films (FIG. 2, red, blue traces) with that of the condensed DAB molecular solid (FIG. 2, inset) indicates that the density of states at binding energies <4.3 eV is dominated by states associate with DAB molecules. Thus, the UPS spectra as well as the core level spectra (FIG. 1) are indicative of composite films composed of intact orthocarborane icosahedra and DAB molecules, with only partial dehydrogenation.

Surface Photovoltage Effect

The surface photovoltage effect is a uniform shift in the valence band spectrum due to exposure to UV light during the photoemission process counteracting the effects of band bending due to hole or electron occupancy of surface states.[4] This shift is thus evidence of delocalization of carriers in the film and is observed upon cross-linking of carborane precursors to form semiconducting films. For orthocarborane films, the surface photovoltage shift is toward lower binding energies upon cross-linking, indicative of a p-type film, with the magnitude of the shift increasing with the amount of induced crosslinking.[4]

Figure 3:
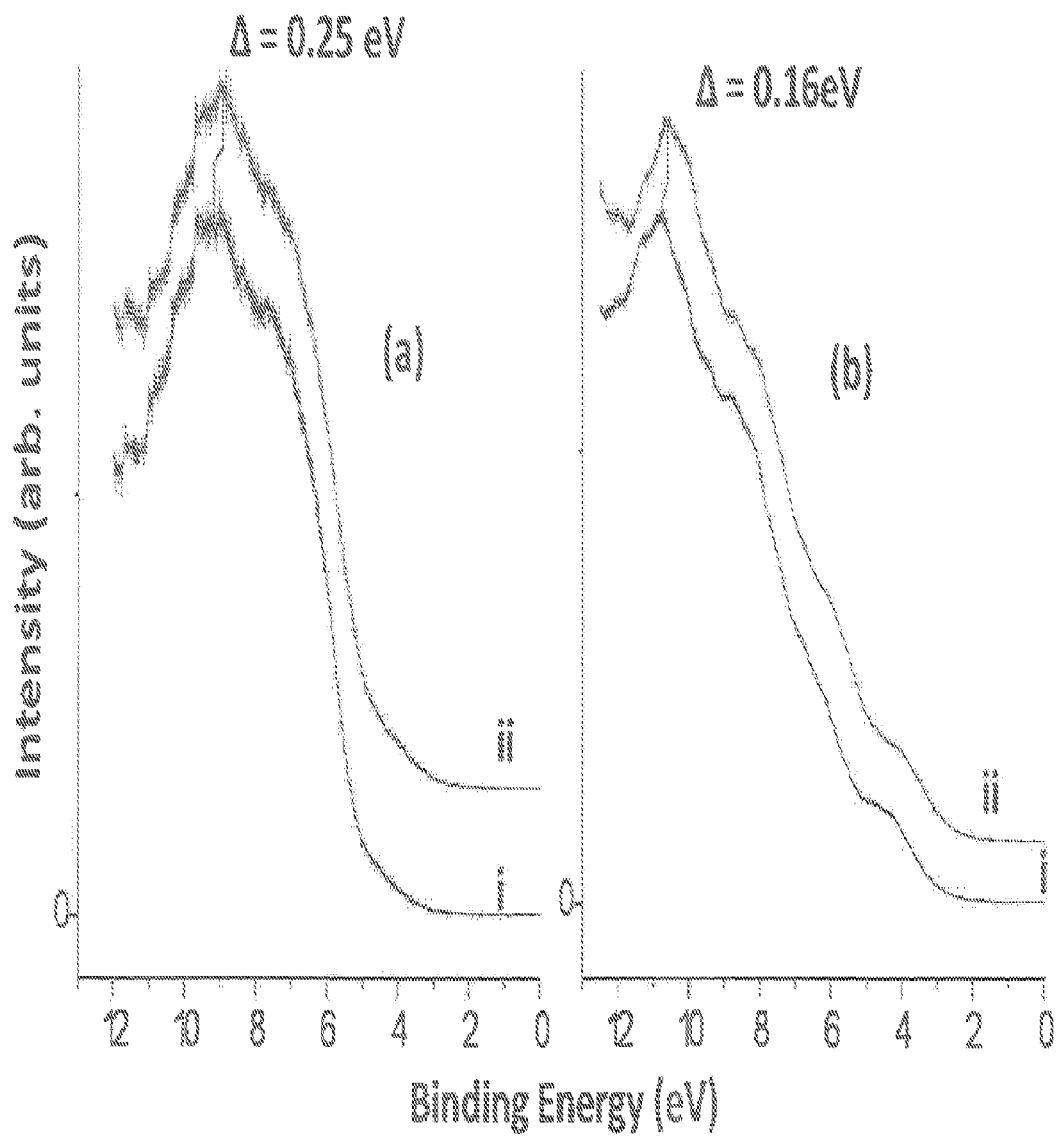
Figure 4:
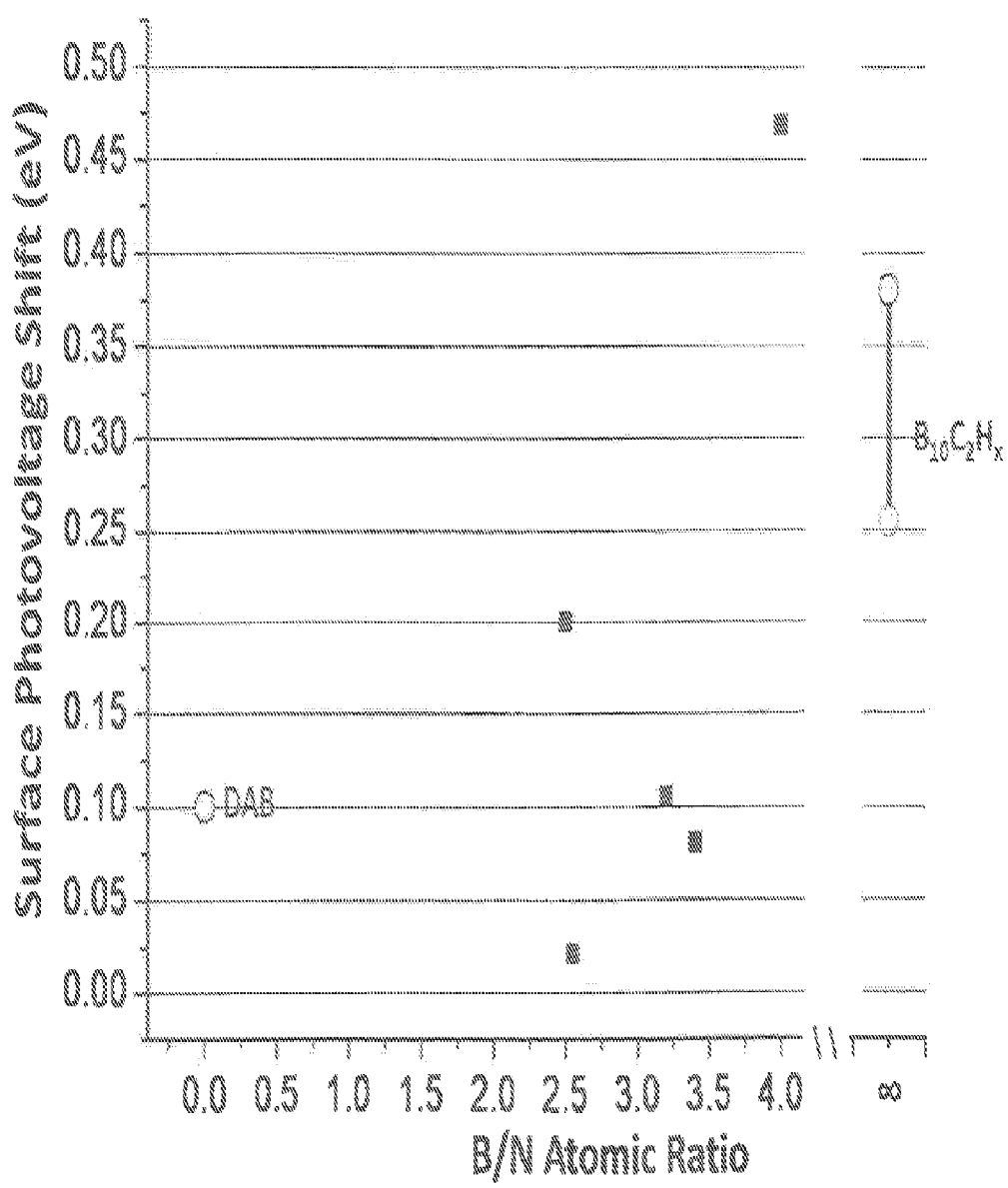
FIG. 4. Surface photovoltage effect as a function of B/N atomic ratio for compound films (closed squares). Shifts for a pure carborane film ($B_{10}C_2H_x$) and a pure DAB film are included for comparison.

UPS spectra are shown in FIG. 3 for both an ortho-carborane (FIG. 3a) and compound film (B/N atomic ratio 3.5; FIG. 3b) before and after electron-induced cross-linking at 110 K. A shift upon cross-linking of 0.25 eV to lower binding energy is observed for the ortho-carborane film, and a shift of 0.16 eV is observed for the compound film. The magnitude of observed shifts upon cross-linking for compound films is plotted against B/N atomic ratio in FIG. 4. There is considerable scatter in the observed shifts—consistent with the variable film thickness and variable extent of intermolecular cross linking. (Slight changes in XPS and UPS spectra were sometimes observed upon warm-up from 110 K to ambient temperature, indicating incomplete cross-linking of condensed species.) The shift, however, is always towards the direction of lower binding energies. In general, the magnitude of the shifts increases with B/N atomic ratio. A shift of 0.46 eV is observed for a compound film with a B/N atomic ratio of 4.1, and this is similar to a shift observed for an ortho-carborane film, although another ortho-carborane film showed a smaller shift (FIGS. 3 and 4). Shifts of this magnitude and direction are also similar to those previously reported[4] for pure ortho-carborane films cross-linked by synchrotron radiation. By comparison, a cross-linked pure DAB film ~40 Å thick exhibits a ~0.1 eV shift in the same direction. Thus, the data in FIG. 4 indicates that at ~1:1 carborane/DAB concentration ratios, the surface photovoltage effect is similar to that of a pure ortho-carborane film, and that at lower relative concentrations, the shift is similar to that observed for DAB. In all cases, however, the direction of the shift is towards lower binding energies, indicative of a p-type film at all observed B/N atomic ratios.

Molecular Orbital Calculations and Simulated UPS Spectra

Simulated UPS spectra are shown in FIG. 5 for an ortho-carborane/DAB molecule bonded via the 2, 3 DAB carbon atoms to B-B-H sites. A comparison of the model calculations of molecular density of states (curves) for the ortho-carborane molecule 5 (a,b), ortho-carborane-DAB molecule in single-bridge bonding configuration 5 (c,d), ortho-carborane-DAB molecule 5 (e,f) in the double-bridging bonding configuration indicates that the addition of DAB leads to an increase in the density of states between the partially dehydrogenated carborane valence band maximum and the chemical potential (the Fermi level of the metallic substrate). Indeed, this additional density of states can be resolved into two features, separated by about 2 eV. This is consistent with what is seen in experiment (FIGS. 2 and 3), where that addition of DAB to the cross-linked film also adds and additional density of states that can be distinguished as two features separated by about 2 eV. This tends to suggest that the carboranes are cross-linked to the DAB by a single boron-carbon bond, not two boron-carbon bonds, as the former better preserves the frontier occupied molecular orbitals of DAB, and thus the additional density of states that can be distinguished as two features separated by about 2 eV.

Discussion

XPS data (FIG. 1) demonstrate that electron-induced cross-linking between ortho-carborane and DAB moieties involves bonding at B-B-H rather than at C-B-H or C-H sites. This is consistent with previously reported[54] gas phase photoionization/fragmentation data for ortho-carborane which indicate that the predominant mechanism for dissociation from an ionized state is the pair-wise elimination of hydrogen from B sites opposite the two carbon atoms in the icosahedrons:

$$B_{10}C_2H_{12} + h\nu \rightarrow [B_{10}C_2H_{12}]^+ \quad (3a)$$

$$[B_{10}C_2H_{12}]^+ \rightarrow [B_{10}C_2H_{10}] + H_2^+ \quad (3b)$$

A similar effect was observed for the vacuum ultraviolet (8.4 eV) exposure of $B_{10}C_2H_x$ films in the presence of $NH_3$, resulting in the attachment of $NH_2$ groups specifically at B-B-H sites.[52] Predominant reaction at B-B-H sites also occurs during the 200 eV electron-induced cross-linking of condensed ortho-carborane films.[38] The reaction to form carborane/DAB bonds at B-B-H sites is therefore consistent with previous data showing that such sites undergo preferential B-H bond scission directly from an ionized state. The B(1s) data in FIG. 1a also indicates that the B-B-H bonds have been replaced by B-B-C bonds, thus shifting the center of gravity of the B(1s) spectrum to higher binding energy, indicating that the composite films involve predominantly ortho-carborane-DAB bonding and are true alloy films, rather than a co-polymer involving large regions of cross-linked ortho-carborane units connected to regions of cross-linked DAB units.

The data in FIG. 1 also indicates that intermolecular bonding involves only C sites on DAB units, leaving the $NH_2$ groups intact. A similar trend is observed in the cross-linking of pure DAB, indicating that C-H bonds preferentially undergo scission upon exposure to 200 eV electrons. Therefore, the data in FIG. 1 indicates that ortho-carborane/DAB alloy films are formed by a site-specific cross-linking process involving B-B-H sites on the ortho-carborane molecule and C-H sites on the DAB molecule.

UPS spectra (FIG. 2) indicates that valence band of the composite film, at binding Energies >4.3 eV is similar to a pure carborane film, but at binding energies <4.3 eV, exhibits features characteristic of a pure DAB film (FIG. 2, inset). This indicates that both the ortho-carborane and DAB moieties retain their molecular identities within the cross-linked composite film. That cross-linking induces true delocalized carriers in the film is evident in the surface photovoltage data (FIGS. 3, 4). If there were neglible interaction between the molecular units in the film, then one would expect no photovoltage effect. If the films were composed of separate regions of cross-linked ortho-carborane and cross-linked DAB units, with a hybrid UPS spectrum, then one would expect a larger shift for the ortho-carborane-dominated portion of the spectrum (>4.3 eV binding energy) and a smaller shift for the DAB-dominated portion (<4.3 eV binding energy). Instead, a uniform shift of the spectrum is consistently observed, indicative of an atomically dispersed, alloyed film with collective, delocalized atomic properties. The photovoltage shift is always towards lower binding energies, indicating that the films are p-type.[4] The magnitude of the shift (FIG. 4) appears to increase with B/N ratio, although there is certainly considerable scatter. The scatter in the data is attributable to the fact that the surface photovoltage effect is known to vary with both film thickness and total degree of cross-linking[4] factors which were difficult to control in the experiments reported here. On the whole, this type of electron beam induced cross-linking has also proved very effective in forming organic dielectric barrier layers that are pin hole free from self-assembled monolayers of terphenyl thiols.[42,55,56,57]

The molecular orbital calculations (FIG. 5) corroborate the conclusion, based upon comparison of experimental UPS data (FIG. 2) that the valence band region at binding energies <2 eV is due to molecular orbitals of primarily DAB character, and that the cross-linked films consist of intact, cross-linked ortho-carborane and DAB moieties. The calculations also indicate the existence of molecular orbitals with substantial combined ortho-carborane and DAB character primarily at binding energies ~5-7.5 eV. The calculations also suggest that the carborane and DAB moieties are connected predominantly by a single boron-carbon bond, rather than by two such bonds.

The results presented here predict that charge transport properties for ortho-carborane/DAB composite films differ substantially from semiconducting $B_{10}C_2H_x$ films. The substantially higher valence band maximum observed for the composite film (FIG. 2) suggest a higher conductivity, certainly of interest for neutron detection and molecular electronics, and Cu/Si CMOS barrier layer applications. The conductivity mechanism(s) for boron carbide films is still a matter of some controversy,[34,58] however, and direct comparisons between $B_{10}C_2H_x$ and composite films may offer some fundamental as well as technological insight. In this regard, there are some distinct differences of these cross-linked molecular films as compared with the electron beam induced cross-linked films formed from the terphenyl thiol self-assembled monolayers. In the latter molecular films, while the band gap decreased with cross-linking,[42] the films actually became mush better dielectrics,[42,55,56,57] and photovoltaic charging increased.

SUMMARY AND CONCLUSION

Compound ortho-carborane/DAB films have been formed by co-condensation of the molecular species and electron beam-induced cross-linking at 110 K. XPS and UPS data indicate that the films consist of intact ortho-carborane and DAB entities cross-linked via B-B-H sites on the ortho-carborane icosahedra and carbon sites on the DAB moiety. The UPS data indicate that the inclusion of DAB in the films over a range of relative B/N concentrations raises the valence band maximum from ~4.3 eV to 1.7 eV below the Fermi level. UPS and molecular orbital calculations indicate that valence band features at binding energies <4.3 eV are dominated by features associated with DAB. The UPS spectra of compound films, however, exhibit uniform surface photovoltage shifts upon cross-linking at 110 K, indicating that the charge carriers exhibit delocalized behavior in the cross-linked films. Experiment and theory, therefore, indicate that the compound films are composed of intact ortho-carborane and DAB species cross-linked with each other, and exhibiting semiconducting, slightly p-type behavior. The decrease in the surface photovoltage effects indicates that the charge carriers that the carrier density increases or that there is an increase in carrier mobility with increasing DAB content.

Neutron Detector Embodiment

The neutron detectors of this invention employ the novel condensation orthocarborane/DAB alloy films of this invention as the p-type layer of the detector. The layer is typically 60-150 Angstroms in thickness, although thickness may be varied to match device performance requirements. A neutron detector typically has ap-type layer sandwiched with an n-type layer. For the neutron detectors of this invention, the inventive polymer alloy maybe combined with an n-type boron carbide as formed, but there are also n-type dopants of boron carbides (Ni, Cr, Mn and Fe; of which Ni is the most robust and most reliable) and also n-type semiconductors like silicon, SiC, GaAs, GaN and BN. Successful neutron voltaics have been made with boron carbide on top of n-type silicon and with p-n junctions made from just boron carbide. Accordingly, the polymer alloy of orthocarborane and DAB condensed and cross-linked pursuant to this invention can be combined with any of the above n-type layers, to give the heterojunction neutron detector desired or further doped with an n-type dopant to create a homojunction boron carbide-diamino benzene solid state diode. As the orthocarborane/DAB layer is preferably formed directly on a metal conductor like copper, the formation surface may serve as a first electrical contact. A second contact is provided opposite, and the neutron detector can be connected in a circuit that is insensitive to thermal neutrons and lighter particles, but readily detects the neutrons emitted from radioactives. The signal generated may be amplified as disclosed in U.S. Pat. Nos. 7,368,794 and 6,771,730

REFERENCES (1) Fox, M. A.; Hughes, A. K. *Coord. Chem. Rev.* 2004, 248, 457.
(2) Ahmad, A., A.; Ianno, N. J.; Snyder, P. G.; Welipitiya, D.; Byun, D.; Dowben, P. A. *J. App!. Phys.* 1996, 79, 8643.
(3) Behera, S.; Wilks, J.; Dowben, P. A.; Kelber, J. A. *Surf Sci.* 2010, 604, L51.
(4) Caruso, A. N.; Balaz, S.; Xu, B.; Dowben, P. A.; McMullen-Gunn, A. S.; Brand, J. I.; Losovyj, Y. B.; McIlroy, D. N. *App. Phys. Lett.* 2004, 84, 1302.
(5) Farha, O. K.; Spokony, A. M.; Mulfort, K. L.; Hawthorne, F. M.; Mirkin, C. A.; Hupp, J. T. *J. Am. Chem. Soc.* 2007, 129, 12680.
(6) Schwab, P. F. H.; Levin, M. D.; Michl, J. *Chem. Rev.* 1999, 99, 1863.
(7) Sevryugina, Y.; Julius, R.; Hawthorne, M. F. *Inorg. Chem.* 2010, 49, 10627.
(8) Yang, X.; Jiang, W.; Knobler, C. B.; Mortimer, M. D.; Hawthorne, M. F. *Inorg. Chem.* 1995, 240, 371.
(9) Yang, X.; Jiang, W.; Knobler, C. B.; Hawthorne, M. F. *J. Am. Chem. Soc.* 1992, 114, 9719.
(10) Caruso, A. N.; Dowben, P. A.; Balkir, S.; Schemm, N.; Osberg, K.; Fairchild, R. W.; Flores, O. B.; Balaz, S.; Harken, A. D.; Robertson, B. W.; Brand, J. I. *Mat. Sci. and Eng.* 2006, 135, 129.
(11) Robertson, B. W.; Adenwalla, S.; Harken, A.; Welsch, P.; Brand, J. I.; Dowben, P. A.; Claassen, J. P. *App. Phys. Lett.* 2002, 80, 3644.
(12) Emin, D.; Aselage, T. *J. App. Phys.* 2005, 97, 013529.
(13) Day, E.; Diaz, M. J.; Adenwalla, S. *J. Phys. D.: App!. Phys.* 2006, 39, 2920.
(14) Caruso, A. N. *J. Phys.: Cond. Matt.* 2010, 22, 443201.
(15) Caruso, A. N.; Billa, R. B.; Balaz, S.; Brand, J. I.; Dowben, P. A. *J Phys.: Cond. Matt.* 2004, 16, L139.
(16) Osberg, K.; Schemm, N.; Balkir, S.; Brand, J. I.; Halbeck, M. S.; Dowben, P. A.; Hoffman, M. W. *IEEE Sens. J.* 2006, 6, 1531.
(17) Osberg, K.; Schemm, N.; Balkir, S.; Brand, J.; Halbeck, S.; Dowben, P. *Proceedings of the 2006 IEEE Symposium on Circuits and Systems (ICAS 2006)* 2006, 1179.
(18) Mortensen, M. W.; Sørensen, P. G.; Björkdahl, O.; Jensen, M. R.; Gundersen, H. J. G.; Bjørnholm, T. *App!. Rad. and Isotopes* 2006, 64, 315.
(19) Luo, G.; Lu, J.; Liu, J.; Mein, W.; Dowben, P. A. *Mat. Sci. and Eng. B* 2010, 175, 1.
(20) von Wrochem, F.; Scholz, F.; Gao, D.; Nothofer, H.; Yasuda, A.; Wessels, J. M.; Roy, S.; Chen, X.; and Michl, J. *J. Phys. Chem. Lett.* 2010, 3471, 3477.
(21) Hwang, S.; Remmes, N. B.; Dowben, P. A.; McIlroy, D. N. *J. Vac. Sci. and Technol. B* 1996, 14, 2957.
(22) Hwang, S.; Remmes, N.; Dowben, P. A.; McIlroy, D. N. *J. Vac. Sci. and Technol. A* 1997, 15, 854.
(23) Carlson, L.; Lagraffe, D.; Balaz, S.; Ignatove, A.; Losovyj, Y. B.; Choi, J.; Dowben, P. A.; Brand, J. I. *Appl. Phys. A.* 2007, 89, 195.
(24) Dowben, P. A.; Kizilkaya, O.; Liu, J.; Montag, B.; Nelson, K.; Sabirianov, I.; Brand, J. I. *Mat. Lett.* 2009, 63, 72.
(25) McIlroy, D. N.; Hwang, S. D.; Yang, K.; Remmes, N.; Dowben, P. A; Ahmad, A. A.; Ianno, N. J.; Li, J. Z.; Lin, J. Y.; Jiang, H. X. *Appl. Phys. A.* 1998, 67, 335.
(26) Liu, J.; Luo, G.; Mei, W.; Kizilkaya, O.; Shepherd, E. D.; Brand, J. I.; Dowben, P. A. *J. Phys. D.: Appl. Phys.* 2010, 43, 085403.
(27) Carroll, R. L.; Gorman, C. B. *Angew. Chem. Int. Ed.* 2002, 41, 4378.
(28) McIlroy, D. N.; Zhang, J.; Dowben, P. A.; Xu, P.; Heskett, D. *Surf Sci.* 1995, 328, 47.
(29) Zhang, J.; McIlroy, D. N.; Dowben, P. A.; Zeng, H.; Vidali, G.; Heskett, D.; Onellion, M. *J. Phys. Cond. Matt.* 1995, 7, 7185.
(30) McIlroy, D. N.; Zhang, J.; Dowben, P. A.; Heskett, D. *Mat. Sci. and Eng. A.* 1996, 217/218, 64.
(31) Caruso, A. N.; Bernard, L.; Xu, B.; Dowben, P. A. *J. Phys. Chem. B.* 2003, 107, 9620.
(32) Balaz, S.; Caruso, A. N.; Platt, N. P.; Dimtcho, I. D.; Boag, N. M.; Brand, J. I.; Losovyj, Y. B.; Dowben, P. A. *J. Phys. Chem. B* 2007, 111, 7009.
(33) Ruhl, E.; Riehs, N.; Behera, S.; Wilks, J.; Liu, J.; Joachim, H.-.; Caruso, A. N.; Boag, N. M.; Kelber, J. A.; and Dowben, P. A. *J. Phys. Chem. A.* 2010, 114, 7284.
(34) Werheit, H. *J. Phys.: Cond. Matt.* 2007, 19, 186207.
(35) Hwang, S.; Yang, K.; Dowben, P. A.; Ahmad, A. A.; Ianno, N. J.; Li, J. Z.; Lin, J. Y.; Jiang, H. X.; McIlroy, D. N. *Appl. Phys. Lett.* 1997, 70, 1028.
(36) Lee, S.; Mazurowski, J.; Ramseyer, G.; Dowben, P. A. *J. Appl. Phys.* 1992, 72, 4925.
(37) Lunca-Popa, P.; Brand, J. I.; Balaz, S.; Rosa, L. G.; Boag, N. M.; Bai, M.; Robertson, B. W.; Dowben, P. A. *J. Phys. D.: Appl. Phys.* 2005, 38, 1248.
(38) Pasquale, F.; Kelber, J. *App. Surf Sci.* 2012, 258, 2639.
(39) Moulder, J. F., Stickle, W. F., Sobol, P. E.; Bomben, K. D. *Handbook of X-ray Photoelectron Spectroscopy*; Physical Electronics: Eden Prairie, Minn., 1995.
(40) Tanuma, S.; Powell, C. J.; Penn, D. R. *Surface and Interface Analysis* 2003, 35, 268.
(41) Practical Surface Analysis, 2nd ed; Briggs, D. Seah, M. P., Eds.; Auger and X-ray Photoelectron Spectroscopy Volume 1; John Wiley and Sons, INC.: New York, USA, 1990; Vol. 1, pp 244-248.
(42) Feng, D.-Q.; Losovyj, Y.; Tai, Y.; Zharnikov, M.; Dowben, P. *J. Mater. Chem.* 2006, 16, 4343.
(43) Xiao, J.; Zhang, Z.; Wu, D.; Routaboul, L.; Braunstein, P.; Doudin, B.; Losvyj, Y. B.; Kizilkaya, O.; Rosa, L., G.;

Borca, C. N.; Gruverman, A.; Dowben, P. A. *Phys. Chem. Chem. Phys.* 2010, 12, 10329.
(44) Xiao, J.; Dowben, P. A. *J. Phys.: Cond. Matt.* 2009, 21, 052001.
(45) Xiao, J.; Sokolov, A.; Dowben, P. A. *Appl. Phys. Lett.* 2007, 90, 242907.
(46) Dowben, P. A.; Rosa, L. G.; Ilie, C. C.; Xiao, J. *J. Elect. Spect. and Rel. Phenom.* 2009, 174, 10.
(47) Xiao, J.; Dowben, P. A. *J. Mater. Chem.* 2009, 19, 2172.
(48) Zhang, Z.; Alvira, J.; Barbarosa, X.; Rosa, L., G.; Routaboul, L.; Braunstein, P.; Doudin, B.; Dowben, P. A. *J. Phys. Chem. C.* 2011, 115, 2812.
(49) Feng, D.-Q.; Wisbey, D.; Losovyj, Y. B.; Tai, Y.; Zharnikov, M.; Dowben, P. A. *Phys. Rev. B.* 2006, 74, 165425.
(50) Jimenez, I.; Sutherland, D. G. J.; van Buren, T.; Carlisle, J. A.; Terminello, L. J.; Himpsel, F. J. *Phys. Rev. B* 1998, 57, 13167.
(51) Jacobsohn, L. G.; Schulze, R. K.; da Costa, M. E. H. Maia; Nastasi, M. *Surf Sci.* 2004, 572, 418.
(52) Bao, R.; Chrisey, D., B. *Thin Sol. Films* 2010, 519, 164.
(53) Bernard, L.; Caruso, A. N.; Xu, B.; Doudin, B.; Dowben, P. A. *Thin Sol. Films* 2003, 428, 253.
(54) Ruhl, E.; Hitchock, A. P.; Bozek, J. D.; Tyliszczak, T.; Kilcoyne, A. L. D.; McIlroy, D. N.; KnopGericke, A.; Dowben, P. A. *Phys. Stat. Sol. B* 2009, 246, 1496.
(55) Zharnikov, M.; Grunze, M., *J. Vac. Sci. Technol. B* 2002, 20, 1793-1807.
(56) Geyer, W.; Stadler, V.; Eck, W. Zharnikov, M.; Golzhauser, A.; Grunze, M. *Appl. Phys. Lett.* 1999, 75, 2401-2403.
(57) Eck, W.; Stadler, V.; Geyer, W.; Zharnikov, M.; Gölzhaüser, A.; Grunze, M. *Adv. Mater.* 2000, 12, 805-808.
(58) Werheit, H. *J. Phys.: Conf Ser.* 2009, 176, 012019.

What is claimed is:

1. A semiconducting alloy polymer comprised of cross-linked orthocarborane ($B_{10}C_2H_5$) and 1,4-diaminobenzene (DAB) wherein said polymer reflects a B/N ratio of about 4.1-5.0.

2. The semiconducting alloy polymer of claim 1, wherein said polymer is in the form of a film of 40-90 Angstrom's thickness.

3. The semiconducting alloy polymer of claim 1, wherein said B/N atomic ratio is approximately 4.9.

4. The semiconducting alloy polymer of claim 1, wherein said polymer is comprised of equal parts co-condensed ortho-carborane moieties and DAB moieties.

5. The semiconducting alloy polymer of claim 4, wherein said orthocarborane moieties and said DAB moieties are bound at B-B-H sites in the orthocarborane icosahedra and carbon sites on the DAB moieties.

6. The semiconducting polymer of claim 1, wherein said polymer is formed by condensing orthocarborane and DAB precursors on a metal substrate, followed by electron beam crosslinking of the condensed materials.

7. A neutron detector comprising the semiconducting alloy polymer of claim 1 as a p-type semiconductor.

8. A neutron detector, comprising the semiconducting alloy polymer of claim 1, in electrical contact with an n-type semiconductor, and wherein said semiconducting alloy polymer and said n-type semiconductor are each in electrical contact with conductive leads to define a circuit.

9. The neutron detector of claim 8, wherein said n-type semiconductor is selected from the group consisting of an n-type boron carbide, boron carbide doped with an n-type dopant, silicon, GaAs, GaN and boron nitride.

10. The neutron detector of claim 9, wherein n-type dopant is selected from the group consisting of Ni, Cr, Mn, Fe and mixtures thereof.

11. The neutron detector of claim 8, wherein said detector is of thickness sufficient to avoid generating a signal in response to thermal neutrons.

12. The neutron detector of claim 8, wherein said circuit outputs a signal in response to passage of a neutron that provides a qualitative indication of the presence of radioactive materials.

13. The neutron detector of claim 8, wherein said circuit outputs a signal in response to passage of a neutron that provides a quantitative indication of the amount of radioactive materials.

14. The neutron detector of claim 8, wherein said circuit provides a signal which is amplified before being detected.

* * * * *